United States Patent
Dornhof

(10) Patent No.: US 12,207,860 B2
(45) Date of Patent: Jan. 28, 2025

(54) ELECTROMEDICAL POWER GENERATOR

(71) Applicant: Erbe Elektromedizin GmbH, Tuebingen (DE)

(72) Inventor: Konstantin Dornhof, Horb am Neckar (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 385 days.

(21) Appl. No.: 17/706,934

(22) Filed: Mar. 29, 2022

(65) Prior Publication Data
US 2022/0313344 A1    Oct. 6, 2022

(30) Foreign Application Priority Data
Mar. 31, 2021    (EP) .................................. 21166329

(51) Int. Cl.
  *A61B 18/12*    (2006.01)
  *A61B 18/14*    (2006.01)
  *A61B 18/00*    (2006.01)

(52) U.S. Cl.
  CPC ...... *A61B 18/1206* (2013.01); *A61B 18/1442* (2013.01); *A61B 2018/00178* (2013.01); *A61B 2018/1226* (2013.01); *A61B 2018/1286* (2013.01)

(58) Field of Classification Search
  CPC ............ A61B 18/1206; A61B 18/1442; A61B 2018/00178; A61B 2018/1226; A61B 2018/1286; H02M 7/53803
  See application file for complete search history.

(56) References Cited

U.S. PATENT DOCUMENTS

| 3,658,067 | A |   | 4/1972  | Bross |
|-----------|---|---|---------|-------|
| 3,675,655 | A |   | 7/1972  | Sittner |
| 4,429,694 | A | * | 2/1984  | McGreevy ......... A61B 18/1206 606/40 |
| 4,617,927 | A |   | 10/1986 | Manes |
| 5,825,256 | A |   | 10/1998 | Tchamov et al. |
| 5,896,070 | A |   | 4/1999  | Tchamov et al. |
| 5,952,862 | A |   | 9/1999  | Tchamov et al. |

(Continued)

FOREIGN PATENT DOCUMENTS

| CA | 2286835 A1 | 10/1998 |
|----|-----------|---------|
| DE | 2023140 A1 | 11/1970 |

(Continued)

OTHER PUBLICATIONS

Extended European Search Report dated Sep. 30, 2021, in corresponding European Application No. 21166329.9, with machine English translation (10 pages).

*Primary Examiner* — Kyle J Moody
(74) *Attorney, Agent, or Firm* — Fitch, Even, Tabin & Flannery LLP

(57) ABSTRACT

A power generator (22) according to the invention is configured in a self-oscillating manner. It comprises two cascode circuits (31, 32), the outputs (A1, A2) of which are connected with a parallel resonant circuit (23) in order to excite it in push-pull manner. The input transistors (33, 35) of cascode circuits (31, 32) are cross-coupled, whereas the control electrodes of the output transistors (34, 36) are connected with non-varying potential. The power oscillator (22) is self-controlled such that the transistors (33-36) comprise lowest switching losses.

16 Claims, 3 Drawing Sheets

(56) References Cited

U.S. PATENT DOCUMENTS

| | | | |
|---|---|---|---|
| 5,990,718 A | 11/1999 | Tchamov et al. | |
| 6,039,734 A | 3/2000 | Goble | |
| 7,896,875 B2 | 3/2011 | Heim et al. | |
| 9,155,585 B2 | 10/2015 | Bales et al. | |
| 10,045,810 B2 * | 8/2018 | Schall | A61B 18/1206 |
| 10,105,172 B2 * | 10/2018 | Johnson | A61B 18/1206 |
| 11,744,632 B2 * | 9/2023 | Ripplinger | A61B 18/1206 |
| | | | 606/41 |
| 2010/0137854 A1 | 6/2010 | Hosier | |
| 2011/0112530 A1 | 5/2011 | Keller | |
| 2011/0245826 A1 | 10/2011 | Woloszko et al. | |
| 2012/0053578 A1 * | 3/2012 | Schall | A61B 18/1206 |
| | | | 606/33 |
| 2014/0148803 A1 | 5/2014 | Taylor | |
| 2015/0305798 A1 | 10/2015 | Garito et al. | |
| 2016/0027084 A1 | 1/2016 | Otero | |
| 2017/0079710 A1 | 3/2017 | Deville et al. | |
| 2017/0202607 A1 | 7/2017 | Shelton et al. | |
| 2017/0238987 A1 | 8/2017 | Fregoso | |
| 2022/0313345 A1 * | 10/2022 | Selig | A61B 18/1206 |

FOREIGN PATENT DOCUMENTS

| | | |
|---|---|---|
| DE | 2901153 A1 | 7/1979 |
| DE | 2910196 B1 | 9/1980 |
| DE | 19780481 T1 | 8/1998 |
| DE | 19780470 T1 | 10/1998 |
| DE | 19719440 C2 | 1/2002 |
| DE | 19719441 C2 | 5/2002 |
| DE | 202008001365 U1 | 6/2008 |
| DE | 602004009293 T2 | 7/2008 |
| EP | 1599146 B1 | 10/2007 |
| EP | 2572669 B1 | 4/2017 |
| EP | 2572668 B1 | 5/2018 |

* cited by examiner

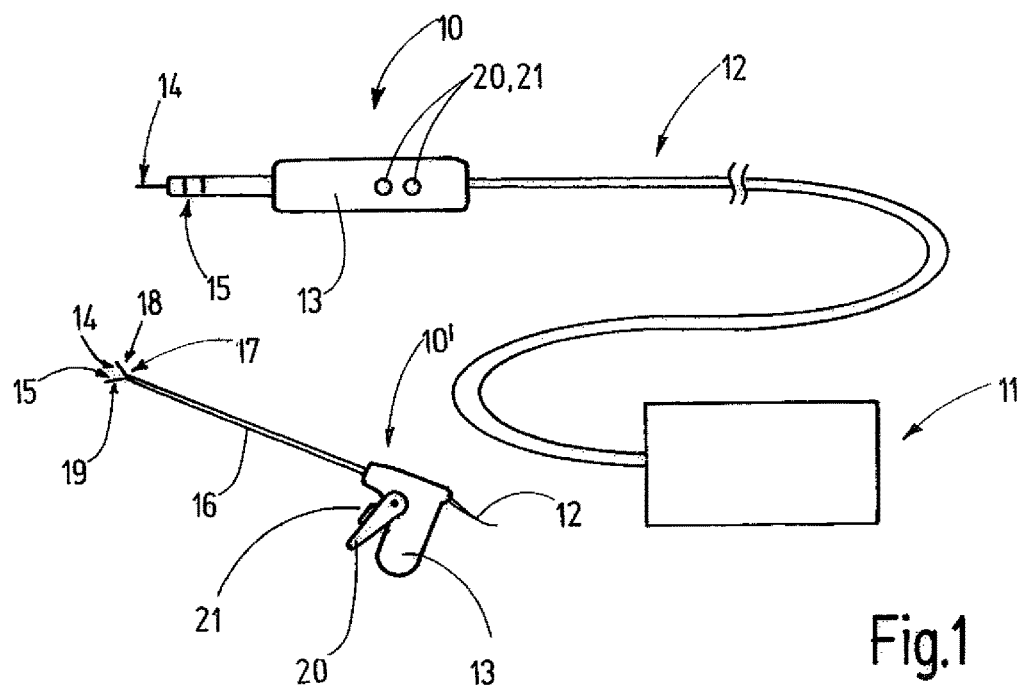
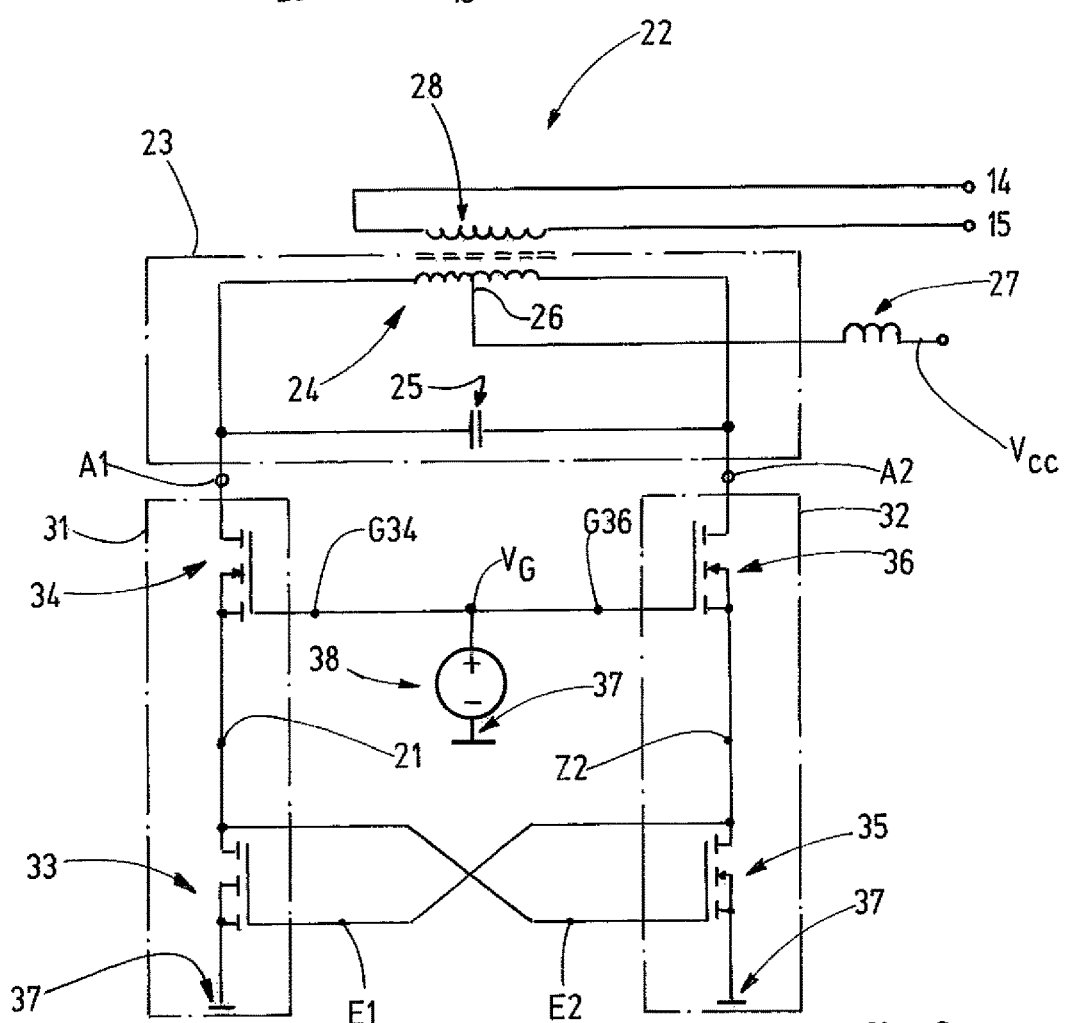
Fig.1
Fig.2

ELECTROMEDICAL POWER GENERATOR

RELATED APPLICATION(S)

This application claims the benefit of European Patent Application No. 21166329.9, filed Mar. 31, 2021, the contents of which are incorporated herein by reference as if fully rewritten herein.

TECHNICAL FIELD

The invention refers to an electromedical generator for supply of one or more electrodes that are provided for carrying out electrosurgical measures on a patient.

BACKGROUND

For avoiding neuromuscular stimulations, in the electrosurgery alternating current having a frequency of remarkably above 100 kHz that has to be provided with a respective power is typically used. Typically the power output is significantly above 1 Watt and can reach multiple 100 Watts. For this purpose respective power generators are required.

Electrosurgical instruments, probes and the like require an electrosurgical generator for supplying the instrument with radio frequency alternating current. For this purpose DE 60 2004 009 293 T2 discloses an electrosurgical system having a generator to which an instrument can be connected that is to be supplied with radio frequency current from the generator. In an embodiment the instrument comprises coagulation electrodes as well as a cutting electrode that are supplied alternatingly in quick sequence in order to concurrently operate therewith. A respective electronic change-over switch is provided in the instrument itself for this purpose.

U.S. Pat. No. 7,896,875 B2 and US 2011/0112530 respectively describe an RF instrument, the external generator of which is supplied by means of a battery. U.S. Pat. No. 9,155,585 B2 describes in addition a battery-operated electromedical generator with externally controlled transistors. An instrument with installed battery and installed generator is known from US 2015/0305798.

Further the use of microwaves for medical treatment is known from EP 2 572 668 B1 as well as from EP 2 572 669 B1. Respective instruments comprise a microwave antenna at the distal end of a longitudinal shank that is supplied from a microwave amplifier arranged in the instrument. The instrument is connected via a cable with a microwave signal generator, the signal of which is guided to the microwave amplifier. In a modified embodiment the microwave signal generator is arranged in the handle of the instrument. A change-over switch then allows the switching between microwave signals of an external signal generator and the microwave signal of the internal signal generator.

An instrument with installed generator is also known from U.S. Pat. No. 6,039,734 that comprises a monopolar electrode for treatment of a patient and closes the current circuit in capacitive manner via the treating person. The operation frequency is higher than 5 MHz. Finally, further prior art is known from US 2017/238987 A1, US 2017/202607 A1, US 2017/079710 A1, US 2016/0270841 A1, US 2014/148803 A1, DE 20 2008 001 365 U1 and CA 2 286 835 A1.

While microwave generators heat and influence tissue by radiation of microwaves, radio frequency operated surgical instruments operate with remarkably lower frequencies. The frequency of currents provided for operation of such instruments is typically at some 100 kHz. Such instruments operate with a radio frequency current flow through the tissue and always require two electrodes in contact with the tissue for this purpose. The instruments serve for carrying out different measures that depend on the current directly flowing through the biological tissue, as for example cutting, coagulating, fusioning, ablating or the like. By means of form and application of respective electrodes, the desired surgical effects can be influenced specifically. Thereby different RF voltages and RF currents are used, just like different modulation forms, e.g. non-modulated RF (CW—"Continuous Wave"), amplitude modulated, e.g. pulsed with or without pulse width modulation and so on and so forth. Moreover, current/voltage dependencies can be defined by means of respective generator output characteristic curves that are beneficial for surgery success.

However, for the operation of such a surgical instrument typically an external surgical generator is required that has to provide the required modes and from which the radio frequency power is transmitted via a cable to the instrument. The modes distinguish, for example, by voltage, current, power, modulation and much more.

DE 29 01 153 A1, US 2010/0137854 A1, US 2011/0245826 A1 and EP 1 599 146 B1 disclose generators with externally controlled switches for exciting of one or more resonant circuits.

Besides medical applications, e.g. in the telecommunication technology, self-oscillating generators are used, as for example known from DE 197 80 481 D1, DE 197 80 470 T1, DE 197 19 440 C2 or DE 197 19 441 C2. These generators are configured as voltage-controlled push-pull-oscillators for ultra/super high frequency range of 1 to 20 GHz. Thereby it shall be operated with a very low operating voltage of, for example, only 4.5 V. The circuits are suitable for the milliwatt range. On the contrary, in the field of electrosurgery one operates with remarkably higher powers and substantially higher voltages. Thereby the danger of voltage overload of individual components exists.

It is one object of the invention to provide a generator circuit that is suitable for the use in electrosurgery and achieves a high efficiency with simple configuration.

SUMMARY

This object is solved with a power generator as described herein.

The power generator according to the invention comprises a resonant circuit that is arranged between the outputs of two cascode circuits. The cascode circuits are connected with one another in feedback (positive feedback) manner and thus form together with the resonant circuit a self-oscillating generator. This concept results in a simple generator configuration in which the high ohmic outputs of the cascode circuit do not impair the quality of the resonant circuit, whereby a good frequency stability and a high spectral purity of the created alternating voltage result. The two cascode circuits operate in a push-pull-manner, whereby due to the alternating positive feedback, switching losses in the two cascode circuits are minimized. The switchover points of time of the individual transistors are defined by the oscillation of the parallel resonant circuit in an ideal manner. By minimizing the switching losses this concept is particularly suitable for generators that output a power suitable for use in the electrosurgery.

The cascode circuits comprise an input transistor in common emitter or common source circuit and an output transistor in common base or common gate circuit in each case. The output transistors operated in common base or common gate circuit can support at their output electrodes (collector or drain) the high voltages occurring at the resonant circuit without danger for the respective output transistor. Also for this reason the generator circuit according to the invention is suitable, particularly for use in the electrosurgery.

The control electrode (base or gate) of the input transistor of a cascode circuit is connected with the output electrode (collector or drain) of the input transistor of the other cascode circuit. The output electrodes of the input transistors are connected with the current inputs (emitter or source) of the output transistors of the cascode circuits. The connection point between the output electrode of the input transistor and the current input of the output transistor forms a tap. At this tap only a low voltage (between 0 and, for example, 20 V) occurs even in case of high operating voltages such that the input transistors are not subject to high voltages at their control electrodes (base or gate). Thus also here the technical effort for protection of the control electrodes is minimized. Additional components, such as diodes or the like, for protection from overvoltages can be omitted. The capacitive load of the control electrodes is minimized, whereby switching flanks with maximum steepness can become effective and in turn switching losses can be reduced.

The control electrodes of the input transistors can be connected with the tap, particularly in capacitive manner. In addition, they can be connected with one another in resistive manner in order to prevent a potential drift and to enforce symmetrical switching between the two cascode circuits.

The control electrodes of the output transistors are preferably connected with a non-varying potential, e.g. ground or a direct voltage. The direct voltage can be derived from the operating voltage. If the transistor is normally conductive, as it is frequently the case for GaN-transistors, for example, the control electrodes can be directly connected to ground.

Particularly this can be realized by means of a linear or non-linear voltage divider that can be, for example, a Zener diode or another element creating a non-varying voltage with regard to a reference potential (ground). Preferably the control electrodes of the output transistors are connected in capacitive manner with the reference potential (ground).

The parallel resonant circuit connected to the outputs of the cascode circuits comprises an inductor having a center tap that is connected with a direct voltage source, preferably via a reactor. The direct voltage source can provide a direct voltage of 100 V, 150 V, 200 V or more, for example. The voltage that has to be supplied to the electrode of an instrument can be picked up by this inductor in transformer manner.

It is possible to modulate the direct voltage, e.g. in that it alternates between a minimum value and a maximum value. A respective configured supply apparatus can be formed outside an instrument, e.g. as stationary apparatus. The generator is simply configured with regard to the circuit and can be directly arranged inside the instrument due to its low power loss. Different operating modes of the instrument, e.g. with non-modulated radio frequency or also with pulsed or otherwise modulated radio frequency, can be selected in that the supply apparatus supplies either a constant direct voltage or a direct voltage alternating between different direct voltage values or oscillating around an average value.

With the concept according to the invention, RF power generators for the electrosurgical use having utmost high efficiency also at frequencies above multiple 100 kHz, e.g. above 500 kHz. Frequencies of up to 4 MHz and above can be created with lowest switching losses, whereby a high frequency stability and good spectral purity can be achieved.

BRIEF DESCRIPTION OF THE DRAWINGS

Details of the invention are derived from the figures, the drawings and the associated description and claims. The drawings show:

FIG. 1 an instrument for electromedical use connected to a supply apparatus, FIG. 2 a power generator for supply of the electrodes of the instrument according to FIG. 1 in a basic illustration, FIG. 3 the power generator according to FIG. 2 in detailed circuit diagram, FIG. 4 voltages output by the power generator according to FIG. 3 in different operating modes in form of a diagram, FIG. 5 the supply apparatus and the power generator in schematic block diagram illustration.

DETAILED DESCRIPTION

Figure 3:
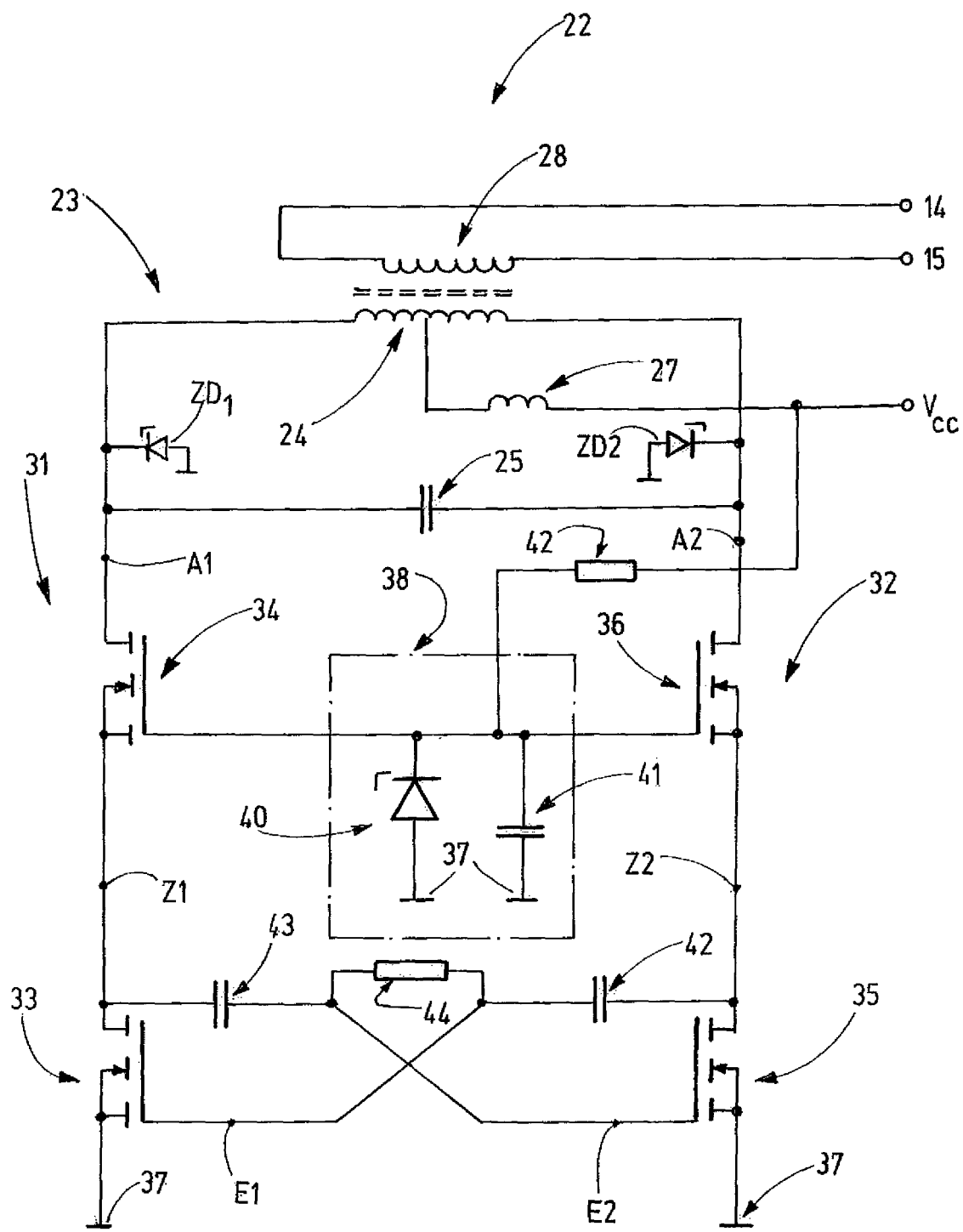

In FIG. 1 an electrosurgical instrument 10 and a supply apparatus 11 are illustrated that are or can be connected with one another by means of a cable 12. The supply apparatus 11 is configured to supply electrical power to the instrument 10 via cable 12. The instrument 10 can be an instrument provided for the open surgical use or an instrument 10' provided for the laparoscopic or other use. For this FIG. 1 illustrates an open surgical and a laparoscopic instrument.

In the present embodiment instrument 10 is operated with direct voltage. The supply apparatus 11 provides a direct voltage, a direct voltage that can be switched on and off, a pulsating direct voltage, a direct voltage oscillating around an average value or also a direct current for the instrument 10. In addition, the supply apparatus 11 can be configured to output an alternating voltage that is then, however, first rectified in the instrument 10 in order to operate a power generator therewith.

The instrument 10 can be an instrument having a handle 13 on which an electrode 14, e.g. a spatula electrode, a needle electrode or the like and as necessary also a counter electrode 15 is provided. Also the instrument 10' provided for the laparoscopic use comprises a handle 13 from which a long slim shank 16 extends away. A tool 17, e.g. in form of a cauterization forceps, is arranged on the distal end of shank 16, the jaws 18, 19 of which support the electrodes 14, 15. On the handle 13 operating elements 20, 21 can be provided for mechanically operating the tool 17 and/or for electrical activation of electrodes 14, 15.

A power generator 22 serves for supply of electrodes 14, 15 that is illustrated in FIG. 2. This power generator 22 is arranged inside instrument 10, 10', as it is preferred, and there preferably inside handle 13. The power generator 22 can, however, basically also be arranged at another location in other embodiments, e.g. in the extension of cable 12, in a connector of cable 12 or inside supply apparatus 11 itself. In this latter embodiment cable 12 guides radio frequency voltage and radio frequency current different to the other embodiments. The instrument 10 can be configured as monopolar instrument. Then it comprises an electrode for the treatment arranged preferably on the distal end and an extensive neutral electrode connected with the instrument via a neutral conductor. It can be configured as adhesive electrode that is attached on the patient for current feedback. In such embodiments the generator can also be arranged in or on the neutral electrode, in the neutral conductor or at any other location mentioned above.

The power generator 22 is schematically illustrated in FIG. 2 for explanation of its components. A resonant circuit 23 consisting, for example, of an inductor 24 and a capacitor 25, that are connected parallel to one another, is part of the power generator 22. This resonant circuit 23 is the frequency determining component of power generator 22. The inductor 24 is preferably provided with a center tap 26 that is connected to an operating voltage $V_{cc}$, as necessary via a reactor 27. The operating voltage $V_{cc}$ can be supplied via cable 12 from supply apparatus 11. The center tap 26 can be arranged exactly in the center, such that the provided two inductor halves have exactly the same inductivity. The center tap 26 can also be arranged slightly "eccentrically", such that the two inductor halves comprise (slightly) different inductivities. This can simplify the oscillation buildup of power generator 22. This can simplify the operation in the pulsed mode.

The inductor 24 can be in magnetic coupling with the decoupling inductor 28 and can form a transformer therewith. The winding ratio of inductor 24 to decoupling inductor 28 is defined according to the requirements of the electrosurgical treatment process and can thus be larger than as well as smaller than one. Also the coupling factor between inductor 24 and decoupling inductor 28 being between zero and one can be defined according to the requirements of the electrosurgical treatment process. Preferably the decoupling inductor forms, together with tissue held between the electrodes 14, 15, a galvanic circuit without branches.

The (parallel) resonant circuit 23 is connected to the outputs 29, 30 of two cascode circuits 31, 32. A first input transistor 33 and a first output transistor 34 are part of the first cascode circuit 31. A second input transistor 35 and a second output transistor 36 are part of the second cascode circuit 32. The transistors 33-36 are switching transistors, preferably field-effect transistors. Basically however, also bipolar transistors, IGBTs or other controlled switches can be used. The following description applies for field-effect transistors and bipolar transistors accordingly under the provision that base, emitter and collector replace gate, source and drain. The presented circuit principle is suitable for p- or n-field-effect transistors of the enhancement type or of the depletion type as well as for pnp- or npn-bipolar transistors.

The first cascode circuit 31 comprises a first input E1, an intermediate tap Z1 and a first output A1. Accordingly, the second cascode circuit 32 comprises a second input E2, a second intermediate tap Z2 and the output A2. The first input E1 is formed by control electrode of the first input transistor 33. If the first input transistor 33 is a field-effect transistor or IGBT, the control electrode is the gate. In the case of a bipolar transistor the control electrode is its base.

The second input transistor 35 also comprises a respective control electrode, e.g. a gate or a base, forming the second input E2.

The first input transistor 33 comprises a source connection that is connected with reference potential, e.g. ground 37. In case of the use of bipolar transistors, the emitter of this first input transistor 33 is connected with ground 37. The same applies accordingly for the second input transistor 35.

The input transistors 33, 35 comprise an output electrode (drain or collector) respectively that forms the intermediate tap Z1 or Z2 and is respectively connected with the current input of the output transistor 34, 36. The current input of the output transistor 34, 36 is its source electrode (or emitter in case of bipolar technology is used) respectively. The control electrodes of the two output transistors 34, 36 are either independent from one another or connected both with a non-varying potential. For this purpose they can be connected with a constant voltage source 38 that supplies a substantially constant potential above the reference potential 37. The control electrodes of the output transistors 34, 36 are their gate electrodes or bases in case of bipolar transistors. If normally conductive transistors are used, the reference potential can also be 0 V (ground).

The drain or collector electrodes of the two output transistors 34, 36 form the outputs A1, A2 of the two cascode circuits 31, 32.

The input E1 is connected with the intermediate tap Z2. The input E2 is connected with the intermediate tap Z1. In doing so, the input transistors 33, 35 together form a flip-flop circuit that is not able to oscillate solely, but rather comprises a bistable character. The downstream output transistors 34, 36 in common gate circuit are concurrently load and clock pulse generator for the flip-flop circuit formed by input transistors 33, 35.

The power generator 22 described so far operates as follows:

For putting the power generator 22 into operation it is supplied with an operating voltage $V_{cc}$ at the center tap 26. It has, for example, an amount of +150 V relative to the reference potential 37 (ground). Other voltage values, e.g. 10 V or each value inbetween, can be used.

After oscillation buildup of power generator 22 an oscillation that is symmetrical relative to the operating voltage $V_{cc}$ phase-shifted about 1800 applies at the outputs A1 and A2. The currents that periodically flow through the output transistors 34, 36 thereby are clock-pulse generators for the flip-flop circuit—consisting of the input transistors 33, 35—that consequently switches in the rhythm of the oscillation of the resonant circuit 23 to and fro. In other words, the input transistors 33, 35 switch alternatingly on and off (they become alternatingly conductive or non-conductive). The approximately squarewave voltages applied on the intermediate taps Z1, Z2 are amplified by the output transistors 34, 36 and thus maintain the oscillation of the resonant circuit 23, even though it supplies current to the electrodes 14, 15 via decoupling inductor 28. This generator turns out to be stable in frequency, whereby it can create an oscillation of high spectral purity.

Depending on the amount of the operating voltage $V_{cc}$ applied to the power generator 22 and/or depending on the winding ratio between inductor 24 and decoupling inductor 28, a voltage is applied to electrodes 14, 15 suitable for coagulation, cutting, ablation, fulguration or tissue fusion or for other purposes. The voltage range can thereby range from below 100 V up to multiple 100 V. Powers in the medium power range between 1 and 100 W as well as powers in the upper power range of 100 W up to multiple 100 W can be achieved. The transistors 33-36 thereby operate in switching operation exclusively with minimum switching losses due to switching precisely and in-phase. The transistors 33-36 switch in the current and voltage-free condition. The power generator 22 is thus very highly miniaturizable. The power loss is in the range of a few watts or fractures of a watt. This particularly applies for frequencies between 100 kHz and 5 MHz.

Due to the supply of the power generator with direct voltage, it is particularly advantageous, if power generator 22 is arranged inside instrument 10, 10'. The electrical conductors present in the cable 12 are subject to direct voltage. By means of reactor 27—as necessary in connection with a not further illustrated buffer capacitor—the current flowing in the cable 12 can be homogenized so far that the superimposed ripple is negligible. This allows the use of non-shielded or only slightly shielded cables that are accordingly flexible and thus simplify the handling of instrument 10.

FIG. 3 illustrates power generator 22 again in a slightly more detailed form. For description thereof the already introduced reference signs and explanations apply accordingly.

The constant voltage source 38 is formed by means of a Zener diode 40 in the present embodiment, the cathode of which is connected with the control electrodes of the output transistors 34, 36 and the anode of which is connected with the reference potential (ground) 37. A capacitor 41 can be connected in parallel to Zener diode 40 in order to connect the signal applied to the cathode of Zener diode 40 in an alternating voltage manner with ground. A resistor 42 can supply the constant voltage source 38 with current and connects the operating voltage connection $V_{cc}$ with the control electrodes (gates) of transistors 32, 34 and the constant voltage source 38 accordingly. Zener diodes ZD1 and ZD2 can connect the outputs A1 and A2 with ground (reference potential 37) and thus secure them against overvoltages.

Further the connection between the input electrode E1 and the intermediate tap Z2 can be realized by means of a coupling capacitor 42. Further a coupling capacitor 43 can realize the connection between the intermediate tap Z1 and the control electrode E2. The control electrodes or control inputs E1, E2 can be connected with one another via resistor 44 in a direct current manner in order to create corresponding potentials at the control electrodes E1, E2 in the time average.

Also in this power generator 22 the resonant circuit 23 is the frequency determining element. The coupling capacitors 42, 43 are on the contrary not frequency determining. They are rather dimensioned so large that the power generator 22 would not operate or only with remarkably lower frequency without the frequency determining resonant circuit.

Figure 4:
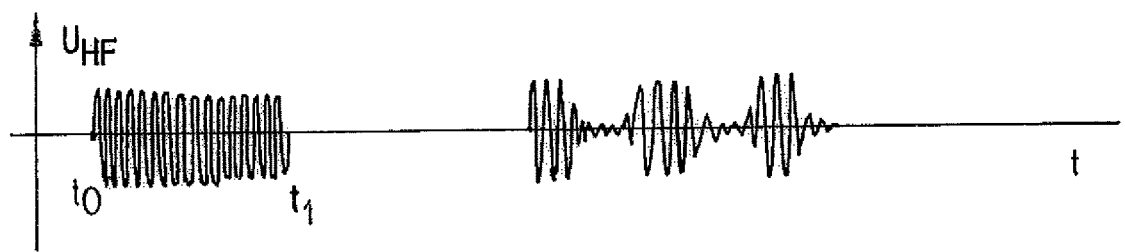

In the description above it has been assumed that the supply apparatus 11 supplies the instrument 10 continuously with direct voltage and direct current. The operating elements 20, 21 can serve as electrical switches in order to selectively connect the power generator 22 with the supply apparatus 11 or isolate it therefrom. In doing so, instrument 10, 10' can be activated or deactivated. For this purpose FIG. 4 illustrates the time-dependent progress of the voltage UHF starting from a point in time t0 at which the power generator 22 is operative up to a point in time t1 at which the power generator 22 is switched off. The period between the points in time t0 and t1 corresponds to the activation of instrument 10, 10'. The RF voltage UHF is applied to the electrodes 14, 15 during this activation substantially unabatedly and continuously.

Figure 5:
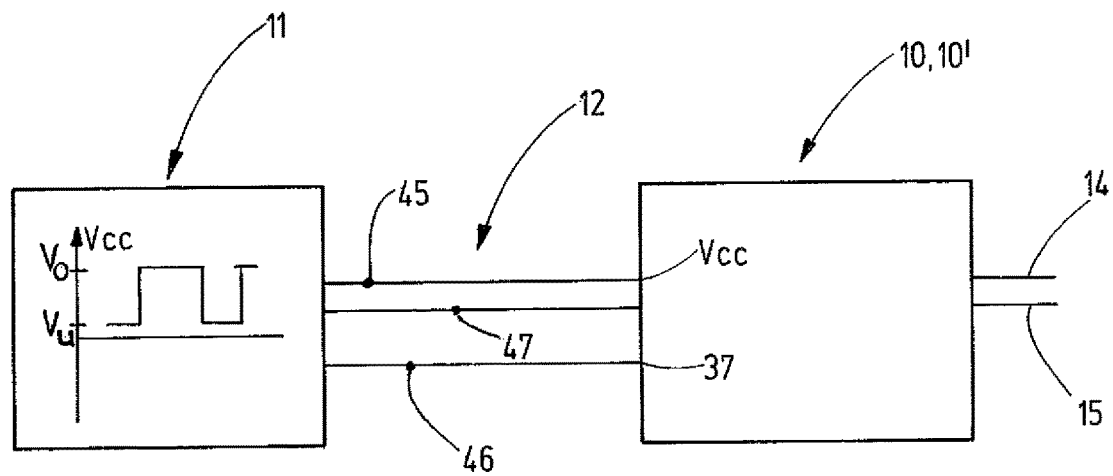

It is however also possible to configure the supply apparatus 11 for output of a pulsating (or otherwise modulated) direct voltage. It can change, for example, between a voltage value of 150 V and a voltage value of 10 V, as illustrated in FIG. 5 on the left side for the supply apparatus 11. The upper voltage value Vo as well as the lower voltage value Vu according to the voltage progress in FIG. 5 can be defined in a non-varying manner to, for example, 150 V and 10 V. Also other voltage values can be used. Also the upper voltage value Vo and the lower voltage value Vu can be adjustable. In the present embodiment the supply apparatus 11 is configured for switching alternation between the upper voltage value Vo and the lower voltage value Vu— a squarewave form is obtained. However, the operating voltage $V_{cc}$ can also have another time-dependent progress, e.g. a saw tooth progress, a triangular voltage progress, a trapezoid voltage progress or a wavy voltage progress (e.g. sinusoidal form+direct voltage component). For the squarewave form of the operating voltage $V_{cc}$ illustrated in FIG. 5 the RF voltage progress illustrated in FIG. 4 is obtained having a narrow band modulation of the radio frequency voltage.

FIG. 5 illustrates also the cooperation between the instrument 10, 10' and the supply apparatus 11 via cable 12. This comprises at least one core 45 supplying the operating voltage $V_{cc}$ as well as a core 46 applied with reference potential 37, i.e. ground. In addition, one or more cores 47 can be provided that serve for transmission of control signals between instrument 10, 10' and the supply apparatus 11. In doing so, it is possible to adjust at the instrument 10, 10', for example, the amount of the operating voltage $V_{cc}$, the modulation thereof (modulation form, modulation depth, modulation frequency etc.).

A power generator 22 according to the invention is configured in a self-oscillating manner. It comprises two cascode circuits 31, 32, the outputs A1, A2 of which are connected with a parallel resonant circuit 23 in order to excite it in push-pull manner. The input transistors 33, 35 of cascode circuits 31, 32 are cross-coupled, whereas the control electrodes of the output transistors 34, 36 are connected with non-varying potential. The power oscillator 22 is self-controlled such that the transistors 33-36 comprise lowest switching losses.

REFERENCE SIGNS 10, 10' instrument
11 supply apparatus
12 cable
13 handle
14, 15 electrodes
16 shank
17 tool
18, 19 jaws
20, 21 operating elements
22 power generator
23 resonant circuit
24 inductor
25 capacitor
26 center tap
27 reactor
$V_{cc}$ operating voltage
28 decoupling inductor
A1, A2 outputs of cascode circuits
31 first cascode circuit
32 second cascode circuit
33 first input transistor
34 first output transistor
35 second input transistor
36 second output transistor
$G_{34}$ control electrode of first output transistor 34
$G_{36}$ control electrode of second output transistor 36
$V_G$ direct voltage
37 reference potential
38 constant voltage source
40 Zener diode
41 capacitor
42, 43 coupling capacitor
44 resistor
45, 46 cores of cable 12
47 further core of cable 12 for control signals
ZD1, ZD2 Zener diodes

The invention claimed is:

1. An electromedical power generator (22) adapted for creation of a radio frequency voltage (UHF) for treatment of biological tissue, the electromedical power generator comprising:
   a resonant circuit (23) that comprises at least one capacitor (25) and at least one inductor (24) that are connected in parallel to each other to form a parallel resonant circuit;
   a first cascode circuit (31) that comprises a first input transistor (33) and a first output transistor (34); and
   a second cascode circuit (32) that comprises a second input transistor (35) and a second output transistor (36);
   wherein the first and second output transistors (34, 36) are connected with the resonant circuit (23) and the first and second input transistors (33, 35) are connected with one another;
   wherein the first cascode circuit (31) comprises a first input (E1), a first output (A1) and a first intermediate tap (Z1);
   wherein the second cascode circuit (32) comprises a second input (E2), a second output (A2) and a second intermediate tap (Z2);
   wherein the first and second outputs (A1, A2) of the corresponding first and second cascode circuits (31, 32) are connected with the parallel resonant circuit (23); and
   wherein the first intermediate tap (Z1) is connected with the second input (E2) and the second intermediate tap (Z2) is connected with the first input (E1).

2. The electromedical power generator according to claim 1, wherein the first and second inputs (E1, E2) are connected with the second and first intermediate taps (Z2, Z1), respectively, in a capacitive manner.

3. The electromedical power generator according to claim 1, wherein the first and second output transistors (34, 36) each comprise a control electrode ($G_{34}$, $G_{36}$) and the control electrodes ($G_{34}$, $G_{36}$) are each connected with a direct voltage ($V_G$).

4. The electromedical power generator according to claim 1, wherein the first and second output transistors (34, 36) are field-effect transistors.

5. The electromedical power generator according to claim 1, wherein the at least one inductor (24) comprises a center tap (26) that is connected with a supply voltage source ($V_{cc}$).

6. The electromedical power generator according to claim 1, wherein the at least one inductor (24) is arranged in a magnetic coupling with a decoupling inductor (28).

7. The electromedical power generator according to claim 6, wherein the decoupling inductor (28) is connected with at least one electrode (14, 15).

8. An instrument (10, 10') in which the electromedical power generator according to claim 1 is arranged.

9. An arrangement comprising:
   the instrument according to claim 8; and
   a supply apparatus (11) configured for output of a constant or pulsating direct voltage ($V_{cc}$).

10. The arrangement according to claim 9, wherein the supply apparatus (11) is configured for producing a direct voltage ($V_{cc}$) alternating between a minimum value (Vu) and a maximum value (Vo).

11. An arrangement comprising:
    the electromedical power generator according to claim 1; and
    a supply apparatus (11) configured for output of a constant or pulsating direct voltage ($V_{cc}$).

12. The arrangement according to claim 11, wherein the supply apparatus (11) is configured for producing a direct voltage ($V_{cc}$) alternating between a minimum value (Vu) and a maximum value (Vo).

13. An electromedical power generator (22) adapted for creation of a radio frequency voltage (UHF) for treatment of biological tissue, the electromedical power generator comprising:
    a resonant circuit (23) that comprises at least one capacitor (25) and at least one inductor (24) that are connected in parallel to each other to form a parallel resonant circuit;
    a first cascode circuit (31) that comprises a first input transistor (33) and a first output transistor (34); and
    a second cascode circuit (32) that comprises a second input transistor (35) and a second output transistor (36);
    wherein the first and second output transistors (34, 36) are connected with the resonant circuit (23) and the first and second input transistors (33, 35) are connected with one another;
    wherein the first cascode circuit (31) comprises a first input (E1), a first output (A1) and a first intermediate tap (Z1);
    wherein the second cascode circuit (32) comprises a second input (E2), a second output (A2) and a second intermediate tap (Z2);
    wherein the first and second outputs (A1, A2) of the corresponding first and second cascode circuits (31, 32) are connected with the parallel resonant circuit (23); and
    wherein the first intermediate tap (Z1) is connected with the second input (E2) and the second intermediate tap (Z2) is connected with the first input (E1);
    wherein the first and second input transistors (33, 35) are field-effect transistors and each comprise a source that is connected with a reference potential (37).

14. The electromedical power generator according to claim 13, wherein the first and second input transistors (33, 35) each comprise a drain that is connected with the first and second intermediate taps (Z1, Z2), respectively.

15. The electromedical power generator according to claim 13, wherein the first and second input transistors (33, 35) each comprise a gate configured as a control electrode, wherein the gates are the first and second inputs (E1, E2) of the first and second cascode circuits (31, 32), respectively.

16. An electromedical power generator (22) adapted for creation of a radio frequency voltage (UHF) for treatment of biological tissue, the electromedical power generator comprising:
    a resonant circuit (23) that comprises at least one capacitor (25) and at least one inductor (24) that are connected in parallel to each other to form a parallel resonant circuit;
    a first cascode circuit (31) that comprises a first input transistor (33) and a first output transistor (34); and
    a second cascode circuit (32) that comprises a second input transistor (35) and a second output transistor (36);
    wherein the first and second output transistors (34, 36) are connected with the resonant circuit (23) and the first and second input transistors (33, 35) are connected with one another;
    wherein the first and second output transistors (34, 36) are field-effect transistors;
    wherein the first cascode circuit (31) comprises a first input (E1), a first output (A1) and a first intermediate tap (Z1);

wherein the second cascode circuit (32) comprises a second input (E2), a second output (A2) and a second intermediate tap (Z2);

wherein the first and second outputs (A1, A2) of the corresponding first and second cascode circuits (31, 32) are connected with the parallel resonant circuit (23); and wherein the first intermediate tap (Z1) is connected with the second input (E2) and the second intermediate tap (Z2) is connected with the first input (E1);

wherein the first and second output transistors (34, 36) each comprise a source that is connected with the first and second intermediate taps (Z1, Z2), respectively.

* * * * *